United States Patent [19]

Stanec et al.

[11] 4,236,528

[45] Dec. 2, 1980

[54] APPARATUS AND METHOD FOR THE QUANTITATIVE MEASUREMENT OF THE ISOMETRIC CONTRACTION OF THE ADDUCTOR POLLICIS MUSCLE

[76] Inventors: Anna Stanec; George Stanec, both of 15 Secor Rd., Scarsdale, N.Y. 10583

[21] Appl. No.: 974,076

[22] Filed: Dec. 28, 1978

[51] Int. Cl.$^3$ ............................................... A61B 5/05
[52] U.S. Cl. ..................................... 128/741; 128/782
[58] Field of Search ................................ 128/740–742, 128/782

[56] References Cited

U.S. PATENT DOCUMENTS

| | | | |
|---|---|---|---|
| 3,420,222 | 1/1969 | Noe et al. | 128/782 |
| 3,565,080 | 2/1971 | Ide et al. | 128/782 X |
| 3,898,983 | 8/1975 | Elam | 128/782 X |

OTHER PUBLICATIONS

Townsend, M. A. et al., *J. Biomechanics*, 1977, vol. 10, No. 3, pp. 183-193.
Brunner, E. A. et al., *Anesthesiology*, Nov. 1969, pp. 466-477.
Thomas, D. H. et al., Amer. Journ. of Med. Electronics, Apr.-Jun., 1964, pp. 96-100.

*Primary Examiner*—Kyle L. Howell
*Attorney, Agent, or Firm*—Posnack, Roberts, Cohen & Spiecens

[57] ABSTRACT

A universal arm board for hand and forearm fixation is provided for exposing part of the forearm at the wrist for the attachment of electrodes for stimulating the ulnar nerve. The palm of the person being tested rests on the arm board and is fixed in position by a lock assuring immobility of the palm and fingers and leaving free only movement of the thumb which is positioned in a thumb ring. The wrist is immobilized by a belt with a Velcro lock leaving free the exposed part of the palmar side of the forearm at the wrist for ulnar nerve stimulation. The proximal part of the forearm rests on a foam arm protector and is immobilized by a belt with a Velcro lock. A force-transducer positioner is attached to the arm board. The positioner allows adjustments to any position required by the anatomical differences of the thumb-hand angle and allows changes in the resting tension of the adductor pollicis muscle. A miniature force transducer is attached to the transducer positioner and to the thumb ring which provides for man-machine connection. The thumb ring immobilizes the thumb in position by a Velcro strap. The method of thumb fixation and the shape of the thumb ring accounts for the anatomical differences of the human thumb. The output signal from the force transducer is proportional to the force of thumb adduction produced by increased isometric tension in the adductor pollicis muscle evoked by stimulation of the ulnar nerve at the wrist.

12 Claims, 18 Drawing Figures

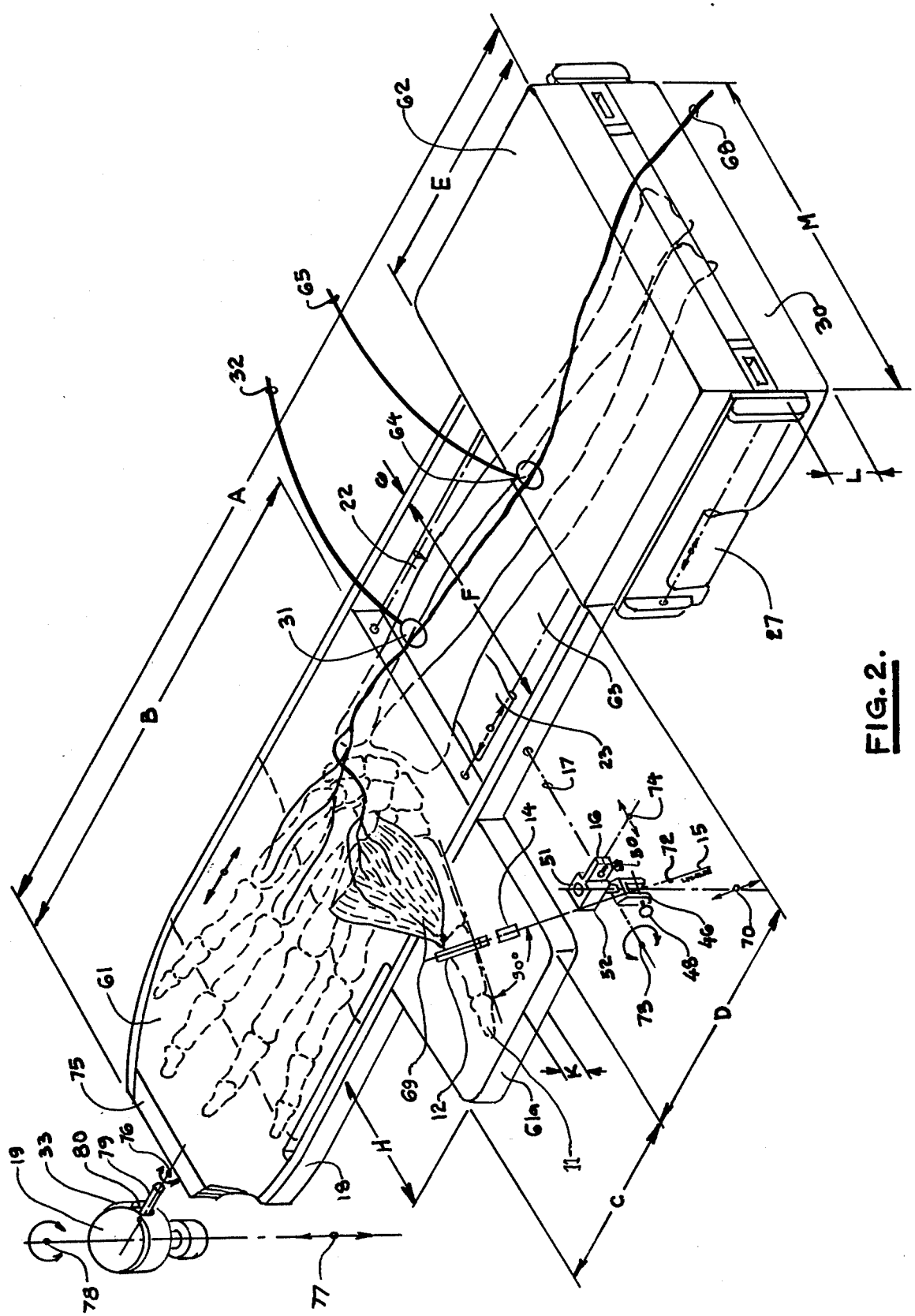

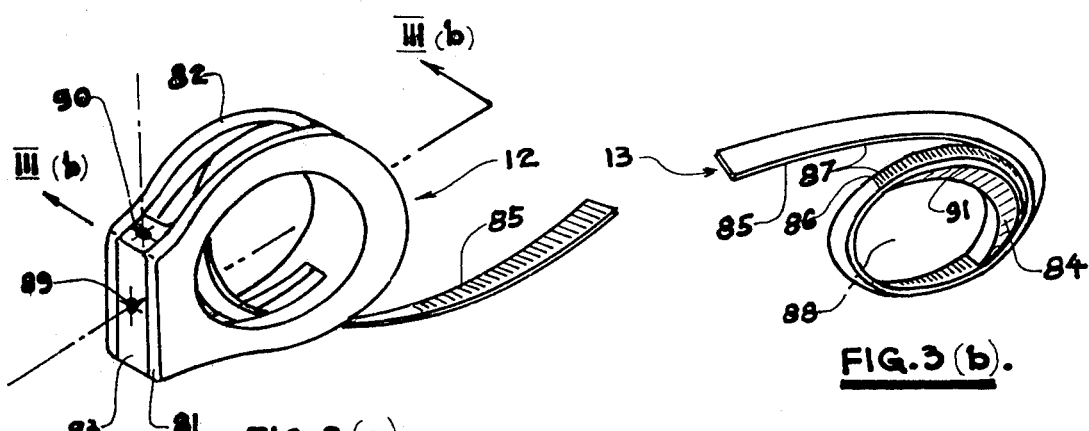
FIG.3(a).
FIG.3(b).
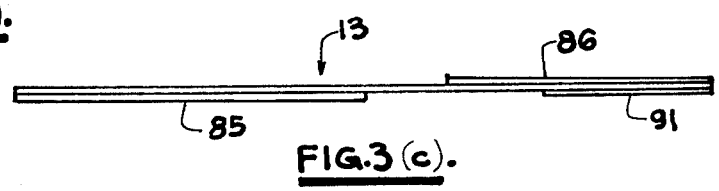
FIG.3(c).
FIG.4(a).
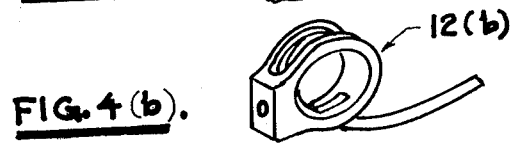
FIG.4(b).
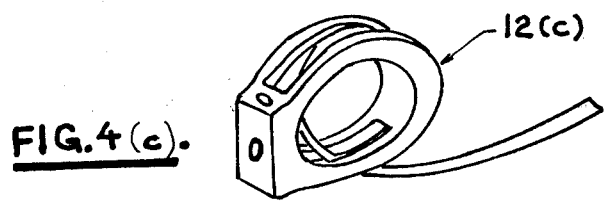
FIG.4(c).
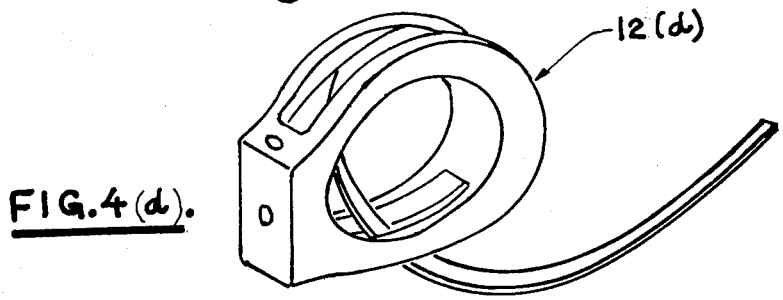
FIG.4(d).
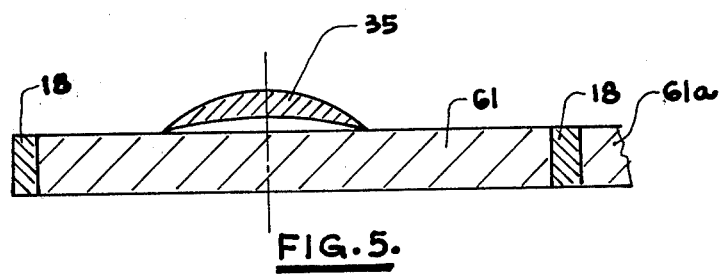
FIG.5.

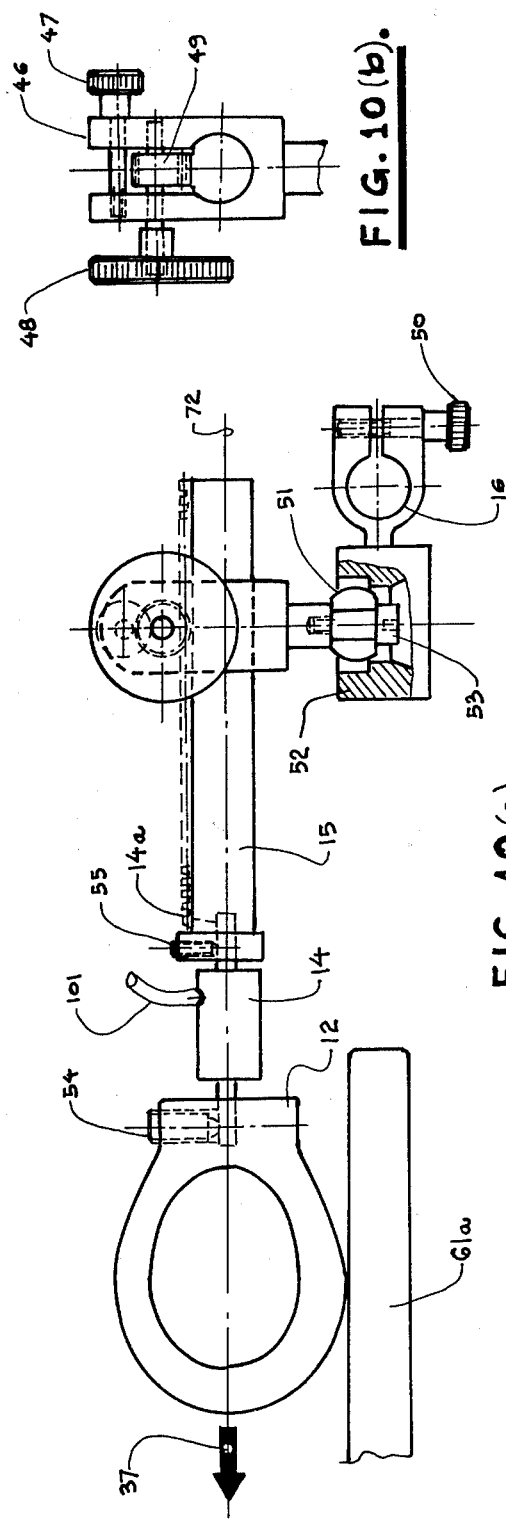
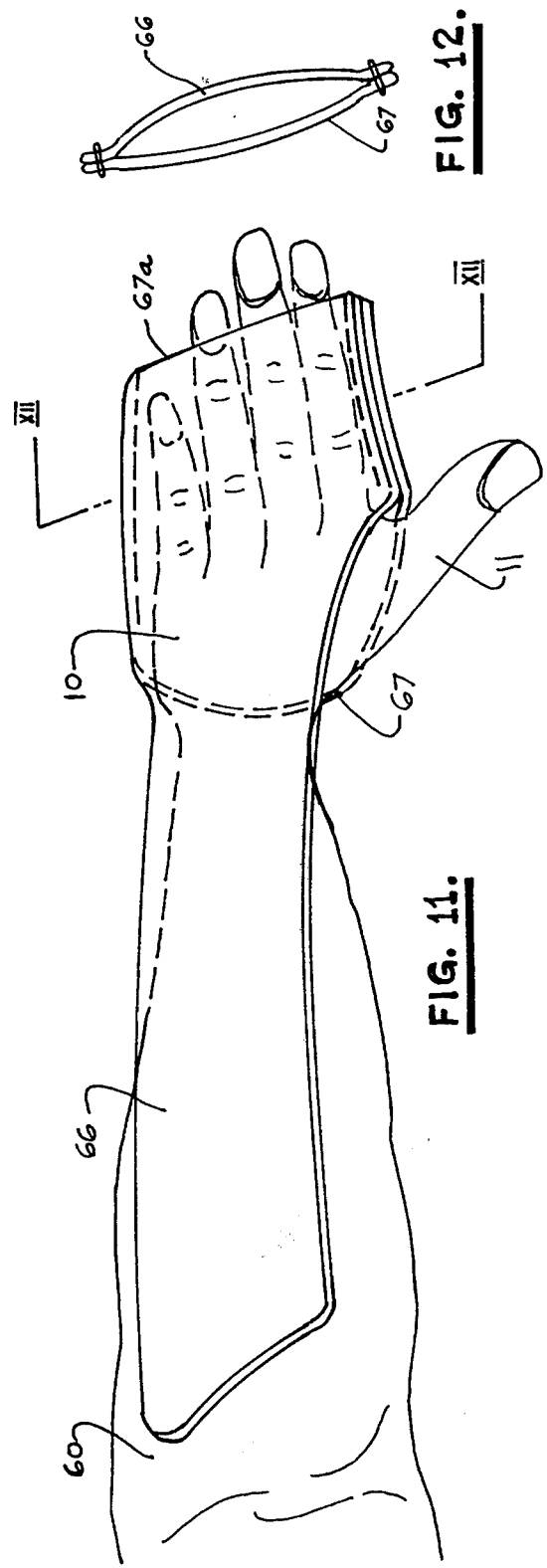

APPARATUS AND METHOD FOR THE QUANTITATIVE MEASUREMENT OF THE ISOMETRIC CONTRACTION OF THE ADDUCTOR POLLICIS MUSCLE

FIELD OF THE INVENTION

This invention relates to methods and apparatus for the quantitative measurement of neuromuscular transmission in the human body and the like and, more particularly, to the measurement of tension developed in the adductor pollicis muscle in response to ulnar nerve stimulation at the wrist of a patient or the like.

BACKGROUND

As will be referred to in greater detail hereinafter, it is known to employ tension measurement techniques with respect to the adductor pollicis muscle of the human body. Known techniques, however, have involved complicated procedures to achieve the positioning of a force transducer in relationship to the anatomy. Because of difficulties, preference has been shown for the monitoring of electrical potentials in the muscle. This, however, is not deemed satisfactory.

Furthermore, an apparatus and method for detecting the degree of muscle relaxation of a medical patient are disclosed in U.S. Pat. No. 3,898,983 which issued to James Elam on Aug. 4, 1975. Therein is discussed a system and method to indicate automatically the degree to which the muscles of a surgical patient have been relaxed by the use of drugs. In accordance with the Elam disclosure, the electrical pulses are applied to the ulnar nerve which causes the fingers of the associated arm to clench. This clenching is detected by an inflatable bladder which is placed in the patient's hands. When the fingers flex, they squeeze the bladder. The resulting change in pressure of a gas in the bladder is detected by a meter which converts the changes into electrical signals, the magnitude of which indicates the degree of muscle relaxation The adductor pollicis muscle is the only ulnar nerve supplied muscle, so that there is reasonable assurance that the same muscle mass is excited by voluntary and electrical stimulation. Also, the ulnar nerve is easily accessible for stimulation due to its superficial location at the wrist. The distance the stimulus has to travel is short and does not introduce complexities related to physiological stimulation. The quantitative measurement of the isometric tension produced by one skeletal muscle as a response to the stimulation of its corresponding motor nerve, represents the events occurring at the neuromuscular junction. Therefore, adductor pollicis muscle supplied by the deep branch of the ulnar nerve is most suitable for studying neuromuscular transmission in man.

Previous attempts have utilized responses of the thumb to which the adductor pollicis muscle as well as ther muscles are attached. Because of technical difficulties associated with thumb and hand positioning and immobilization in relation to different transducers and to anatomical differences of human thumb and hand, the monitoring of the potentials from the muscles of the hand has been preferred or the actual movement of fingers or of the thumb produced by multiple muscles of the hand has been measured in the past. These measurements will pick up the gross qualitative changes in the reactions of muscle groups supplied by the branches of the nerve which is being stimulated. However, in none of the previous patents or publications were the conditions for measurement of isometric contraction of adductor pollicis muscle achieved. Therefore, the most important physiological requirement for quantitative measuremnt of skeletal muscle tension was omitted.

SUMMARY OF INVENTION

In the present invention, apparatus is specifically designed for adductor pollicis muscle isometric tension measurements. The apparatus only measures tension in one muscle evoked by stimulation of one corresponding nerve. We are concerned with studying the truly isometric tension developed by a specific muscle with no movement of the thumb to which the muscle is attached. By "isometric," we mean the development of force by a muscle due to contraction of the muscle fibers without any changes in the physical length of the muscle. The muscle contraction is brought about by electrical stimulation of the nerve innervating said muscle. During isometric contraction of the adductor pollicis muscle with the angle of the thumb-hand joint unchanged, the individual muscle can be expected to contract with constant force and the increases or decreases in the force of contraction will quantitatively measure the effects of different drugs or other stimulating or depressant agents and their interaction at the neuromuscular junction, altering transmission of impulses from nerve to muscle. Our apparatus is designed for measuring the isometric tension of the adductor pollicis muscle as a response to physiological stimulation of a corresponding ulnar nerve. Therefore, changes in isometric tension are responses to changes in neuromuscular transmission. We do not study the function of muscles in relation to the motion of extremities or other parts of the body. We are interested in quantitative measurement of normal, potentiated or depressed transmission of impulses from motor nerve to skeletal muscle and as a tool for this we use the measurement of tension developed in a muscle under isometric conditions, or, in other words, without movement.

According to other aspects of the invention, thumb engaging or supporting means may be provided in a form to encircle the thumb. Said engaging means includes means to prevent displacement between the thumb and said engaging means. Further, said engaging means may be of a construction defining an opening through which said thumb is adapted to extend. The engaging means and, transducer moreover, cooperatively define a structure extending generally perpendicular relative to the thumb and this structure is adjustable to fully abduct said thumb.

In accordance with a feature of the invention, said structure may include a rack and pinion to displace said engaging means to thereby abduct said thumb. Also provided a pivot means about which said transducer and engaging means are pivotable. Said pivot means may include a substantially universal pivot and may further or separately include a pivot defining a pivot axis adapted to be at least substantially parallel to the thumb.

According to other features of the invention, there may be provided means to lock said rack and pinion in fixed position. Moreover, said engaging means may include a rigid frame defining an opening and, in said frame and adapted to be at least generally in intersecting relation with said opening, an adjustable strap for engaging the thumb and avoiding relative movement between said thumb and engaging means. This strap may include cooperating Velcro parts to provide for fastening the strap to itself in a closed loop for adjustable engagement of the thumb.

Holding means are also provided to hold the arm and hand in substantially immobile position thereon. There may be provided, for example, a transparent plastic and generally planar element and a metal frame encircling the same. An extension may be provided on the element which is coplanar and generally perpendicular thereto support the thumb. On the holding means may be provided at least one belt for engaging the arm. The support may be of elongated construction and means may be provided supporting said belt for longitudinal displacement along said support. The belt may be of adjustable construction and may particularly include Velcro parts enabling adjustable engagement of the arm. In accordance with the invention, the aforesaid support may have opposite faces to accommodate the arm selectively, depending on whether the subject or patient is right handed or left handed and means may be comprised to support the belt for utility on either of the said faces selectively.

According to another feature of the invention, cushions may be provided on the opposite faces of the support to protect the arm. Furthermore, in accordance with the feature of the invention, means may be supplied to apply electrical stimulation to the nerve which was mentioned hereinabove. Means may, moreover, be provided on the support for connecting the latter to a fixed reference structure such as a bed or a wall or the like.

A palm support means may be provided in accordance with the invention upon which the palm of the hand of the patient is adapted to rest. This palm support means may be, for example, of a part spherical shape. As an alternative, the palm support means may include a suction means for engaging the aforesaid support with a strap being supplied on the palm support means to connect the same to said hand.

According to another feature, a pillow may be provided detachably connected to the support for immobilizing the hand in monitoring position. Flexible leads may furthermore be provided which provide a flexible connection to the transducer means for carrying the signal therefrom. The support may be provided with an opening through which the nerve can be stimulated.

In accordance with the method of the invention a technique is proivded for measuring the isometric tension of the adductor pollicis muscle developed in response to the electrical stimulation of an associated ulnar nerve, said muscle being located in the palm of a hand and attached to the thumb of said hand on an arm, said method comprising immobilizing said hand and fully abducting thumb and immobilizing said thumb, coupling said thumb to a transducer with the thumb fully abducted, said transducer being adapted to convert said isometric tension into corresponding signals, and electrically stimulating said nerve. Said transducer is preferably arranged at least substantially perpendicular to the thumb.

The above and other objects, features and advantages of the invention will be found in the following detailed description of a preferred embodiment of the invention as illustrated in the accompanying drawing.

BRIEF DESCRIPTION OF DRAWING

In the drawing:

FIG. 2 is an anatomical schematic view of the palm side of the hand and forearm in position with the thumb abducted showing the relationship between the boney structures, ulnar nerve divisions, and supply of the deep branch of the ulnar nerve to the adductor pollicis muscle;

FIG. 3(a) is a perspective view of a thumb engaging means employed in accordance with the invention and as shown in FIG 1;

FIG. 3 (b) illustrates the strap element of the structure of FIG. 3 (a) along line III (b)—III (b) with the strap structure inverted;

FIG. 3 (c) illustrates the strap in stretched out condition detached from the thumb engaging apparatus of FIG. 3(a);

FIGS. 4, (a),4(b),4(c) and 4(d) respectively illustrate different sizes of thumb engaging structures which may be employed in accordance with the invention to accommodate anatomical differences of different age groups and size groups of patients;

FIG. 5 is a schematic sectional view corresponding to a view taken along section line V—V of FIG. 1;

FIG. 10 (a) is a front view of the support, transducer, and engaging devices of FIG. 1;

FIG. 10 (b) is an end view of part of the apparatus illustrated in FIG. 10 (a);

FIG. 11 is a perspective view of a mitten covering for an arm intended to be measured in the apparatus of FIG. 1; and FIG. 12 is a schematic view corresponding to a sectional view taken along cross-sectional lne XII—XII in FIG. 11.

DETAILED DESCRIPTION

According to the invention, the tension developed in an adductor pollicis muscle in response to ulnar nerve stimulation is quantitatively measured. The output signal from the force transducer is used as an input signal to standard recording systems with the use of polygraphs or computerized monitoring systems. For indirect stimulation of the ulnar nerve, any standard stimulator with a stimulus isolation unit may be used. The device and method disclosed herein for quantitative measurement of isometric contraction of the adductor pollicis muscle in man or the like has useful application in the following medical fields:

a. Anesthesiology—monitoring of neuromuscular block during surgery and the return of normal neuromuscular transmission after the use of muscle relaxants.
b. Neurology—measurement of abnormal neuromuscular transmission in patients with neuromuscular disorders.
c. Intensive care medicine—monitoring of neuromuscular transmission in patients on long term ventilatory therapy requiring the use of muscle relaxants and so forth.

d. Clinical pharmacology—studies of drug interaction affecting neuromuscular transmission and new muscle relaxants effects on neuromuscular transmission.

e. Clinical physiology and pathophysiology—studies of normal and fatigued neuromuscular transmission in man.

The present invention can be used, for example, for left or right handed human adults, and for pediatric or newborn patients, as well as independently of different body positions during anesthesia and surgery, or in awake man. The device is adjustable to any position of a bed, chair, or operating room table. It is a portable unit not limited to a specific location of the individual to be monitored.

Figure 1:
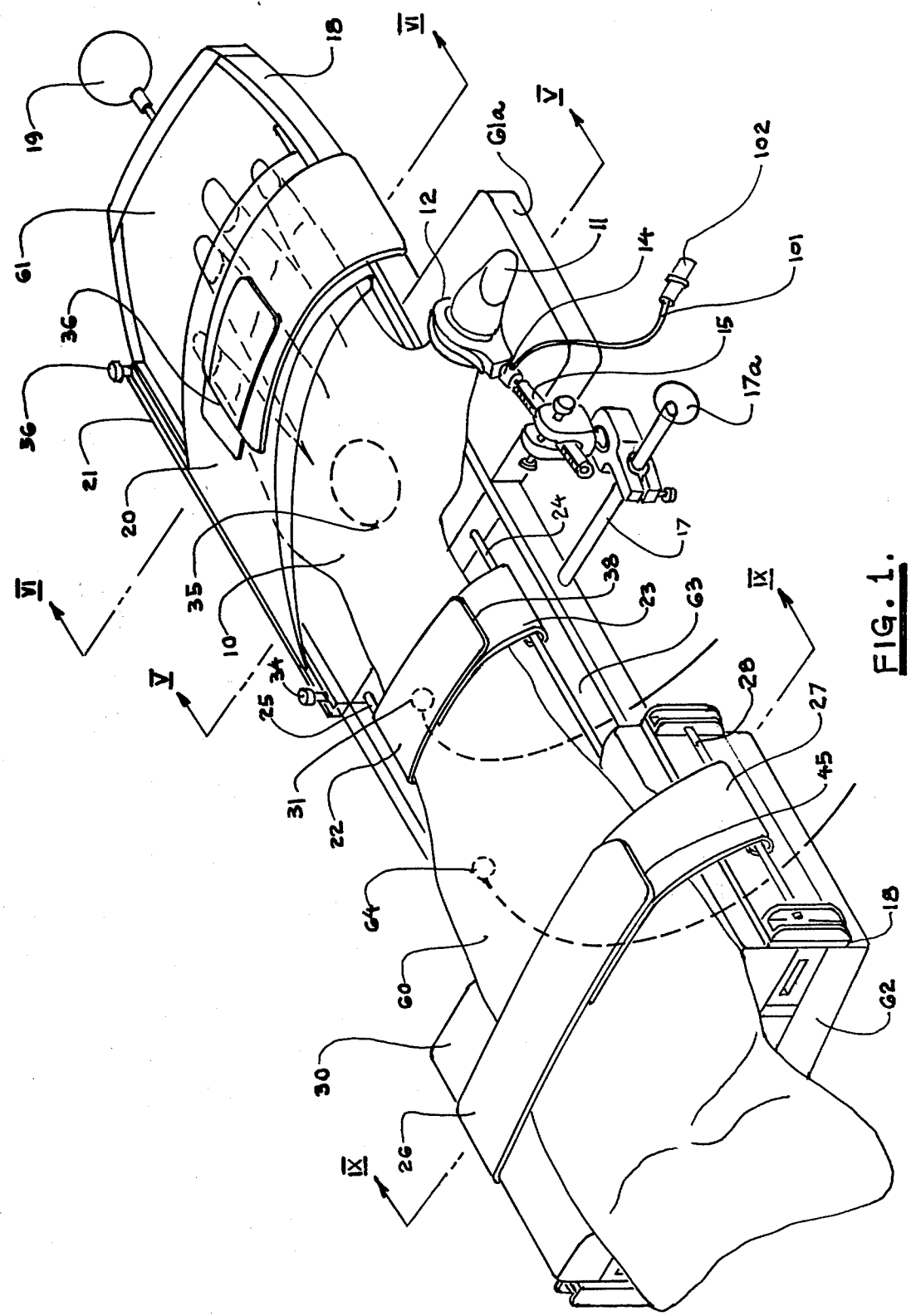
FIG. 1 is a perspective view of an arm board provided with a thumb engager and force transducer in accordance with one embodiment of the invention.

FIG. 1 is a perspective view of the system of the present invention. It shows the back 10 of an adult human hand having a thumb 11 in full abduction and the back 60 of the associated forearm. Hand 10 and the distal part of forearm 60 rest on a support including a metal frame 18 bordering a transparent planar plastic element such as plexiglass body 61. The proximal part of the forearm rests on a forearm protector 30 made of foamy rubber or plastic. The forearm protector is a disposable pad or cushion resting on metal frame 18. An open space 63 in the frame exposes the palm side of the distal end of the forearm for attachment of the electrodes 31 and 64. The hand is immobilized in position with a textile pillow 20 and a Velcro lock 36. In FIG. 1, the pillow 20 is shown in use for a left hand. The right hand pillow is a mirror image of the left hand pillow. Detailed description of this pillow and hand fixation is discussed hereinafter with reference to FIGS. 6, 7 and 8. The palm of the hand rests on a palm support 35 manufactured of plastic or rubber and of a part spherical shape. The details of support 35 are described hereinafter in relation to FIG. 5.

The wrist, positioned above the open space 63, is immobilized by a textile belt strap 22 with a Velcro cushion and a textile belt strap 23 with a Velcro lock. They form a Velcro cushion/lock connection 38. On the exposed palm side of the wrist and distal end of the forearm, the two electrodes 31 and 64 are attached for stimulation of the ulnar nerve. Either superficial skin electrodes or subcutaneous needle electrodes can be used. Textile belt 22 is freely movable along a metal pin 25 and textile belt 23 is freely movable along a metal pin 24. This allows adjustment to different sizes and shapes of the human wrist and forearm. The proximal end of the forearm is immobilized in position with a textile belt 26 having thereon a Velcro cushion and a textile belt 27 with a Velcro lock thereon. They form a Velcro cushion/lock connection 45. Textile belt 26 is freely movable on a metal pin 29 and textile belt 27 is freely movable on a metal pin 28. Details of the forearm immobilization are described hereinafter relative to FIG. 9.

The thumb holding in full abduction is inserted into a thumb ring or support 12. The details of the thumb ring 12 are described hereinafter relative to FIGS. 3 and 4. The thumb ring 12 is connected to a miniature force transducer 14. The transducer 14 has a coaxial cable 101 which ends with a plug connector 102 for connection to recording instrumentation (not shown). The details of the connection between the force transducer 14 and the thumb ring 12 and also between the force transducer 14 and the precision rack 15 are shown in FIG. 10 which depicts the force transducer positioner. The force transducer positioner moves freely on a metal clamp post 17 which is attached to the metal frame 18.

FIG. 1 shows a patient's left forearm and left hand being used for the monitoring of neuromuscular transmission in an adult human being. When right forearm and hand are used, the right arm tests on the back side of the Plexiglass 61 and the forearm 60 rests on the forearm protector 62. The position of the right palm becomes a mirror image of the left hand palm on the metal frame 18 and plexiglass 61. The pillow 20 for a right hand is a mirror image of the same pillow for the left hand. The hand and the forearm are in a mitten made of foam material as later discussed relative to FIG. 11, but not included in FIG. 1 for clarity of the drawing.

FIG. 2 is an anatomical scheme of the palm side of the left hand and left forearm with the stimulation electrodes 31 and 64 in place for indirect stimulation of the ulnar nerve 68 and measurement of changes in tension of adductor pollicis muscle 69 responsible for the thumb 11 adduction. Electrode 31 has a cable connection 32 and electrode 64 has a cable connection 65.

The purpose of FIG. 2 is to show the function of the transducer positioner. The details of this positioner are shown in FIG. 10. The invention assures that the transducer is aligned perpendicular to the fully abducted thumb and perpendicular to the point of insertion of the muscle which is the base of first phalanx of the thumb on the ulnar side. The force of adduction is applied in the axis of the transducer.

The thumb is placed in full abduction in the thumb ring 12 connected to the transducer positioner at a 90° angle. A constant optional resting tension is applied in each case by the use of knurled knob 48 and precision rack 15. Precision pinion shaft 49 is inserted in rack fork 46. The knurled knob 48 turns the precision pinion shaft 49 which moves the precision rack 15 as indicated by arrows 70. The rack fork 46 is inserted in a ball bearing 51. The above-described arrangements allow the thumb ring 12 to slide freely on the plexiglass support 61a. This accounts for adjustment to different anatomical sizes of human hand. Furthermore, the ball bearing block 52 is connected to the split hub clamp 16 which can slide on a clamp post 17, allowing the setting of the position of the thumb with thumb set screw 50 at a 90° angle to the axis 72 of the force transducer with the transducer positioner. The split hub clamp 16 allows setting the ball bearing block 52 in circular direction shown by arrows 73 around the clamp post 17 and in direction shown by arrows 74 parallel to clamp post 17.

FIG. 2 also shows a plexiglass ball 19 inserted in a ball joint 33. This arrangement serves for the support of the hand and forearm in elevated position during the monitoring of neuromuscular transmission, independent of body positions. The ball 19 has a clutch connection to the metal frame 75, which allows turning the ball 19 in a circular direction as shown by arrows 76, if applied torque is greater than the torque set on the clutch. The torque is set in range from 0.050 to 0.150 N-m. A separate ball joint 33 for the ball 19 is attached to any kind of standard support commonly used in hospital rooms, operating rooms, intensive care units or doctors' offices. The vertical movement of the ball joint 33 indicated by arrows 77 is achieved by conventional means. The rotating movement of the ball joint 33 is indicated by arrows 78. The connection of the while arm board to the ball joint 33 is achieved by passing the clutch shaft 79 through a slot 80. The ball 19 then rests in the ball joint 33 during the monitoring. In some cases, the ball 19 during stimulation will act as a handle to keep the device in stable position.

For practical purposes three basic sizes of the device are considered as being depicted in Table I below:
 a. A universal adult device for monitoring neuromuscular transmission in humans.
 b. A universal pediatric device for monitoring neuromuscular transmission in children.
 c. A universal newborn device for monitoring of neuromuscular transmission in normal and premature newborns.

The size of the newborn device has an application also in non-invasive monitoring of neuromuscular transmission in some mammals with similar anatomy of the upper extremity in particular in apes.

TABLE I

| SIZE in mm | A | B | C | D | E | F | G | H | K | L | M |
|---|---|---|---|---|---|---|---|---|---|---|---|
| ADULT | 460 | 220 | 90 | 120 | 120 | 100 | 8 | 75 | 12 | 50 | 170 |
| PEDIATRIC | 240 | 125 | 50 | 60 | 60 | 50 | 6 | 35 | 10 | 50 | 100 |
| NEWBORN | 110 | 60 | 25 | 25 | 25 | 35 | 4 | 20 | 8 | 30 | 80 |

FIGS. 3(a),(b) and (c) show the thumb ring 12 (and included elements) which serve as one of the most important parts of the present device and presents the machine-man connection in the present invention. The function of the thumb ring 12 is to provide a stable and adjustable connection between the human thumb and the miniature force transducer.

The body of the thumb ring 12 consists of plastic flanges 81 and 82, the plastic half moon 84, and the metal end connector 83. The plastic flange 81 and 82 are cast in one piece with the half moon 84. The end connector 83 is bounded by flanges 81 and 82. The plastic used for flange 81 and 82 and the half moon 84 has a property of thermal conductivity as human tissue does. An example of this plastic material is "Duralay" used in dental work. The metal end connector 83 has an opening 89 for the shaft of force transducer 14. Perpendicular to the opening 89 is a threaded connection 90. The threaded connection 90 is used by socket head set screw (FIG. 10). The socket head set screw 54 secures the shaft of force transducer 14.

As to Velcro strap 13, part of this strap as indicated at 91 is self-adhesive and is fastened to the half moon 84. It can be easily peeled off and replaced as needed for sterilization purposes. The part of the strap 13 indicated at 86 has a Velcro lock and the part indicated at 85 has a Velcro cushion. The strap 13 is a standard product of the Velcro Company.

When the thumb 11 is inserted into the thumb ring space 88, the strap 13 presses the thumb against the half moon 84. The strap 13 is then manipulated to form a Velcro cushion/lock connection 87. The thumb 11 then rests comfortably immobilized in the half moon 84. The thumb response to the changes in isometric contractions of the adductor pollicis muscle 69 is instantaneous without a significant dead band. With the compression of the thumb 11 against the half moon 84 due to an applied tension on strap 13 in the range of 250 gr. to 500 gr. for an adult and 25 gr. to 50 gr. for newborns babies, virtually all the dead band is eliminated.

An important feature of the present invention is that it provides a means of quantitive monitoring of neuromuscular transmission under physiological conditions. The described thumb ring 12 represents a man-machine connection previously not available for ths type of monitoring in man. The present arrangement of thumb immobilization in the thumb ring 12 allows a stable connection with the miniature force transducer without applying excessive power to compress the thumb 11 against the half moon 84 and also allows intermittent release of the strap 13 to prevent possible disturbances in blood supply to the thumb during monitoring. It should be further noted that, in accordance with the invention, selected sizes of thumb rings are employed to cover the anatomical differences of various age groups. For example, inside hole sizes of 10 mm to 40 mm may be provided as shown by FIGS. 4(a),(b),(c) and (d) at 12 (a),(b),(c) and (d) respectively.

FIG. 5 shows section of palm support 35. The palm support 35 has a round or spherical shape and is manufactured from plastic or rubber and preferably semi-hard rubber. The palm support 35 has a suction cup connection which allows for changes in location on the plexiglass body 61 as required by the anatomical differences of the human palm. The palm support 35 elevates the palm (e.g., by 8 mm to 12 mm so that adductor pollicis muscle 69 is left free without interference with the immobilization of the hand provided by the belt straps 22 and 23 and by the pillow 20.

Figure 6:
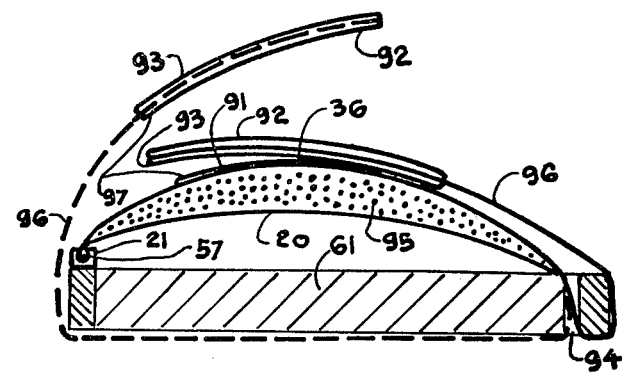
FIG. 6 is a schematic view corresponding to a sectional view taken along line VI—VI of FIG. 1.

FIG. 6 shows a schematic section of the pillow 20 for immobilizing the hand and fingers in monitoring position. The pillow 20 is adapted for freely sliding in a channel 21 and is held in channel 21 by a steel pin 57. The channel 21 is attached to metal frame 18 by a thumb screw 56 and a thumb screw 34, shown in FIG. 1. Pillow 20 is filled with plastic gravel 95 or equivalent material. This provides a better fitting to different shapes of the back of the human hand. The textile belt 96 is pulled through a slot 94 in plastic body 61.

The belt 96 has a Velcro cushion 92 and a Velcro cushion 93 attached to it. To the top of the pillow 20, a Velcro lock 91 is attached. The Velcro cushion 93 and the Velcro lock 91 form a Velcro cushion/lock connection 36. For adjustment to different sizes of hands, two alternative methods fixation are available, as shown in this figure by full line and by dotted line. The full line represents a Velcro cushion/lock connection 36. The dotted line represents a Velcro cushion/lock connection 97.

Figure 7:
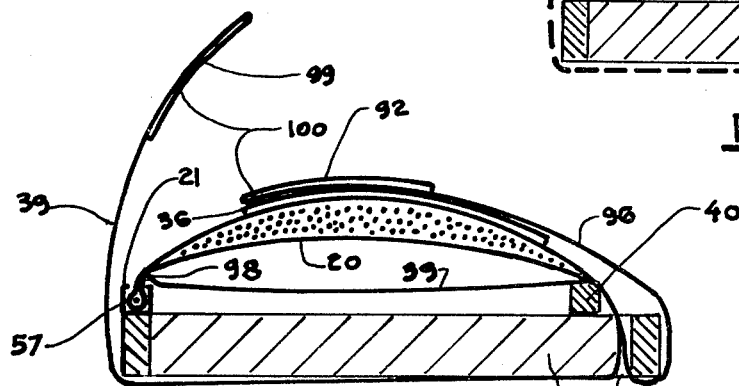
FIG. 7 is a view corresponding to FIG. 6 illustrating a variation thereof.

FIG. 7 shows an alternative arrangement for freeing the adductor pollicis muscle during monitoring without the palm support 35 described in FIG. 5. The belt 39 is sewed on at point 98. The finger belt passes over the top 40 through the slot 94. At the end of the belt is Velcro lock 99. After hand immobilization as described in FIG. 6, the belt 39 lifts the palm from the plexiglass body 61 against the pillow 20 and forms a Velcro cushion/lock connection 100.

Figure 8:
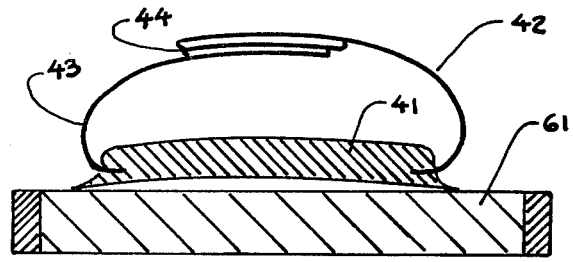
FIG. 8 illustrates a modification of the palm side hand support element illustrated in FIG. 1 corresponding to FIG. 6.

FIG. 8 shows an alternative for hand immobilization on The plexiglass body 61. A suction cup base 41 is manufactured from rubber such as a semi-hard rubber. To the base 41, a textile belt with a Velcro cushion 42 and a textile belt with a Velcro lock 43 is attached. They form Velcro cushion/lock connection 44, securing the hand to the suction cup base 41.

The hand is immobilized in the followng manner: The palm side of the hand is placed on the suction cup base 41 and the side belts 42 and 43 form a tight connection with the hand and the fingers. The palm side of the hand with the suction cup 41 attached to it is placed on the plexiglass body 61 and pressed down against it by applying pressure onto the back of the hand. The attachment, formed by suction of the suction cup base 41 on the plexiglass body 61, immobilizes the hand for monitoring.

Figure 9:
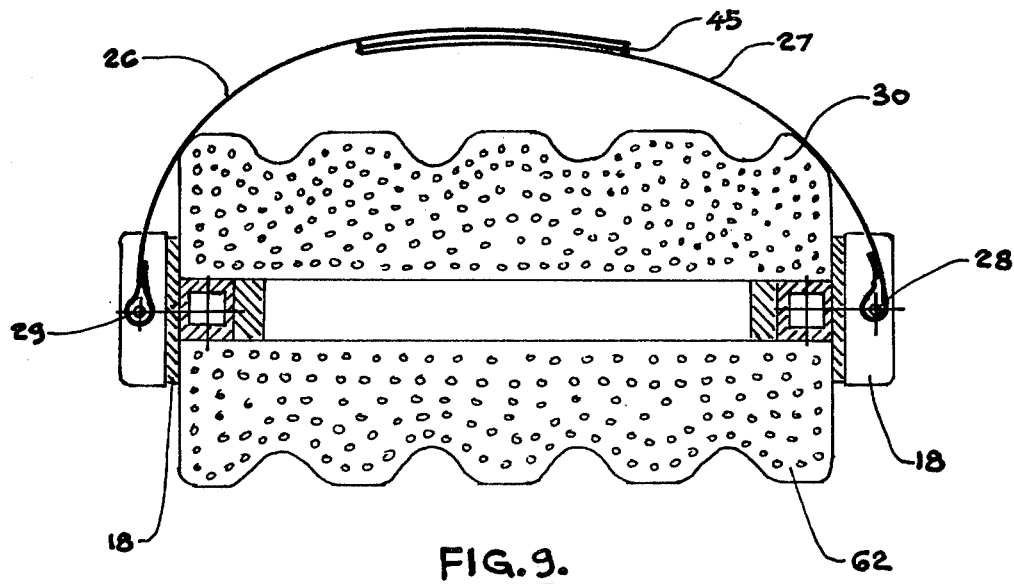
FIG. 9 is a schematic view corresponding to a section along line IX—IX in FIG. 1.

FIG. 9 is a diagrammatic sectional view of the arrangement for the immobilization of the proximal part of the forearm. The forearm 60 is placed on the forearm protector 30 for the left hand or 62 for the right hand. FIG. 9 shows arrangement for left forearm immobilization. The forearm protectors 30 and 62 are each manufactured from non-slip foam resting on and possibly connected to metal frame 18. It is a disposable item called "eggcrate" cushioning pad which is commercially available.

FIGS. 10 (a) and (b) show the force transducer positioner attached to the miniature force transducer 14 which is further attached to the thumb ring 12. The force transducer positioner includes the precision rack 15 extending through the rack fork 46. The rack is driven by precision pinion shaft 49. The precision pinion shaft 49 is connected to knurled knob 48. The thumb set screw 47 is inserted in rack fork 46 and is used to immobilize the precision rack 15 in desired position. The rack fork 46 is inserted in a ball bearing 51 and is immobilized by a shoulder screw 53. The ball bearing 51 is pressed in a ball bearing block 52. The ball bearing block 52 is connected to the spit hub clamp 16. The thumb set screw 50 immobilizes the split hub clamp 16 in desired position on the clamp post 17 shown in FIG. 2.

The socket head set screw 55 holds in position the shaft end connection 14a of the miniature force transducer 14. The socket head set screw 55 is set to release the end shaft of the force transducer 14 if the applied axial force indicated by arrow 37 exceeds 15 kp. The socket head set screw 54 holds the thumb ring 12 in desired position and is set to release the thumb ring 12 if applied axial force indicated by arrow 37 exceeds 12 kp.

The force transducer 14 is an electric miniature force transducer used in conjunction with electronic instruments for the measurment of forces. The measurements are performed without significant movement. This type of miniature force transducer is manufactured for the exact measurement of tensile forces where miniature dimensions are necessary. The applied force is transduced to the measuring body whose force-proportional deformation is converted by four full-bridge strain gauges into a force-proportional electrical signal. It is preferred, that a special make of the measuring body be used in the force transducer so that shearing forces will be substantially eliminated without influencing measuring accuracy. The effect of temperature can be minimized with the circuitry used. The preferred miniature force transducer is water proof.

The specification of the preferred miniature force transducer is as follows:

| | |
|---|---|
| Sensitivity | 1.4 mV/V ± 0.5% |
| Deviation in linearity | ± 0.15% ref. to nominal load |
| Reproducibility | ± 0.1% ref. to nominal load |
| Error with max. 10% shearing force | ± 0.5% |
| Overload capacity | 1.3 × nominal load |
| Measuring stroke with nominal load | Lower than 0.1 mm |
| Range: | |
| Adult | 0–10 kp |
| Pediatric | 0–5 kp |
| Newborn | 0–1 kp |

The type of miniature force transducer used in the system of the present invention (e.g., 717 D-001 or 717D-005) is commercially available on special order from a number of manufacturers such as, for example A. M. Erichsen, GmbH, 5600 Wuppertal 2, West Germany.

FIG. 11 shows a human hand 10 and forearm 60 inserted in an extended mitten formed by sewing from a foam towel which is a disposable item. The mitten consists of the top part 66 of the mitten and of the palm part 67 of the mitten. These parts are sewed together as shown in section in FIG. 12, leaving the thumb free outside of the mitten.

One purpose of the mitten is to cushion the hand and the forearm in the device and, in particular, to cushion the back of the forearm against the belts 27 and 26. Another purpose is to cushion the back side of the wrist against the belts 22 and 23. Still another purpose is to cushion the back side and the palm side of the hand against the pillow 20 and the plexiglass body 61. The foam of the mitten also absorbs moisture on the palm side of the hand. The mitten is formed with an opening at 67a to leave the fingers free. The purpose of leaving the fingers free as shown in this figure is to allow observation of the immobilized fingers during monitoring. The material from which the mitten is manufactured can be sterilized or used as a disposable item. Different sizes of the mittens can be prepared in sizes similar to regular commercially available mittens to fit various age groups.

While various features have been discussed hereinabove, there are still further features which should be noted in accordance with the invention. Thus, for example, in FIG. 1 is shown a knob 17a adapted for being threaded on the end of support 17. This knob is capable of being detached from the rod 17 to commit the ready detachment of the support on which is mounted the transducer. It should be noted that the rod 17 lies generally parallel to the thumb 11 and that the transducer and thumb engaging means form with the support a structure which generally lies perpendicular to the rod or support 17 thereby enablng displacement of the same in parallel with the axis of the thumb and in parallel with the axis of the rod 17 while this structure extends preferably and generally substantially perpendicularly relative to the axis of the thumb 11.

It will also be noted that the arm board includes a perpendicular portion 61a extending in generally coplanar relationship to the arm board or body 61 while extending perpendicularly thereof to accommodate the thumb 11. By reason of the fact that the arm board has opposite faces, the location of the extension 61a will enable the different faces to constitute mirror images of one another such that it is readily possible to accommodate right handed or left handed patients or the like without any difficulty whatsoever.

There will now be obvious to those skilled in the art many modifications and variations of the structure set forth hereinabove. These modifications and variations will not however depart from the scope of the invention if defined by the following claims.

With respect to the method of the invention, it will be appreciated from what has been started above, that the invention provides a method for measuring the isometric tension of the adductor pollicis muscle associated with a thumb and developed in response to electrical stimulation of the associated ulnar nerve, said method comprising fully abducting said thumb, coupling said thumb to a transducer with the thumb fully abducted, and electrically stimulating the ulnar nerve. It will be noted that when the ulnar nerve is stimulated according to the illustrated embodiment discussed hereinabove, this develops isometric tension in the adductor pollicis muscle and this isometric tension is measured and is directed to a computer or is otherwise displayed such as, for example, on an oscilloscope or the like.

What is claimed is:

1. Apparatus for engaging a hand and thumb on the forearm of a human subject or the like and for measuring quantitative changes in isometric tension in the associated adductor pollicis muscle in response to stimulation of the associated ulnar nerve, said apparatus comprising engaging means for engaging and immobilizing said hand, thumb holding means having an opening alignable generally perpendicular to the thusly engaged hand for receiving and holding said thumb, transducer means operatively associated with said thumb holding means for converting isometric tension developed in said adductor pollicis muscle in response to said ulnar nerve stimulation into an electrical signal, and adjustable positioning means to adjust the positioning of said thumb holding means and the alignment of said opening so that said thumb can be immobilized in fully abducted position and so that said transducer means can measure the isometric tension in the the adductor pollicis muscle.

2. Apparatus as claim in claim 1 wherein said engaging means includes a section for engaging and immobilizing the forearm in alignment with the thusly engaged and immobilized hand.

3. Apparatus as claimed in claim 2 wherein said thumb holding means includes a generally ring-like structure defining said opening and belt means on said structure to encircle and immobilize the thumb in said opening.

4. Apparatus as claimed in claim 3 wherein said belt means is a Velcro strap passing through said ring-like structure in intersecting relation with said opening and adapted for self-engagement in the form of an adjustable closed loop.

5. Apparatus as claimed in claim 3 wherein the transducer means is connected to the thumb holding means on the adjustable positioning means and said adjustable positioning means includes means for adjusting the distance of the thumb holding means from said engaging means and the relative position of the the thumb holding means along said engaging means, and angular disposition of the thumb holding means relative to said engaging means.

6. Apparatus as claimed in claim 5 wherein said engaging means includes a structure having a generally flat surface on which said forearm and hand can rest, an extension on which the thumb can rest, and straps on the latter said structure for holding the arm and hand immobile thereon, the latter said structure being provided with an opening adjacent the juncture of the arm and hand to provide for the application of ulnar nerve stimulation.

7. Apparatus as claimed in claim 6 wherein the means included by said adjustable positioning means includes a rod extending from the structure of said engaging means, a clamp slidable along and rotatable on said rod, pivot means to hold said thumb holding means and transducer means.

8. Apparatus as claimed in claim 6 wherein said engaging means includes an adjustable palm support means on said flat surface, said palm support means being of a part spherical shape.

9. Apparatus as claimed in claim 8 wherein said engaging means includes adjustable finger stop means to limit movement of the hand upon abducting of the thumb.

10. Apparatus as claimed in claim 3 wherein said transducer means extends generally radially from said ring-like structure.

11. A method for meassuring isometric tension of the adductor pollicis muscle of a thumb having an associated ulnar nerve, said muscle being located in the palm of the hand on an arm of a subject, said method comprising immobilizing said hand and fully abducting and immobilizing said thumb, coupling said thumb to a transducer with the thumb fully abducted, said transducer being adapted to convert isometric tension of said muscle into corresponding signals, and electrically stimulating said ulnar nerve.

12. A method as claimed in claim 11, comprising arranging said transducer at least substantially perpendicular to the immobilized thumb in full abduction thereby providing for quantitative measurement of standardized resting tension of said muscle and for accurate quantitative measurement of truly isometric tension of said muscle under physiological conditions.

* * * * *